United States Patent [19]

Trivedi

[11] Patent Number: 4,837,207

[45] Date of Patent: Jun. 6, 1989

[54] DIASTEREOISOMERS OF N6-ENDO-BICYCLO[2.2.1]HEPTYLADENOSINE AS ANTIHYPERTENSIVES WITH SELECTIVE ACTION

[75] Inventor: Bharat K. Trivedi, Canton, Mich.

[73] Assignee: Warner-Lambert Company, Morris Plains, N.J.

[21] Appl. No.: 49,178

[22] Filed: May 13, 1987

[51] Int. Cl.$^4$ .................... A61K 31/70; C07H 19/167
[52] U.S. Cl. ........................... 514/46; 514/45; 514/47; 536/24; 536/26
[58] Field of Search ............... 514/45, 46, 47; 536/24, 536/26

[56] References Cited

U.S. PATENT DOCUMENTS 3,838,147  9/1974  Pohlke et al. .................. 536/26
4,714,697 12/1987  Trivedi ......................... 514/46

OTHER PUBLICATIONS

Ts'O (editor) "Basic Principles in Nucleic Acid Chemistry", vol. 1, Academic Press, N.Y., 1974, pp. 115, 159 and 160.
U.S. Ser. No. filed 9-9-85.
EPO Search Report with attachments.

*Primary Examiner*—Ronald W. Griffin
*Assistant Examiner*—L. Eric Crane
*Attorney, Agent, or Firm*—Joan Thierstein

[57] ABSTRACT

(1R-endo) or (1S-endo)-N-bicyclo[2.2.1]heptyl adenosine and pharmaceutically acceptable acid addition salts having highly desirable antihypertensive properties and unexpected $A_1$ and $A_2$ receptor binding activity, processes for their manufacture and pharmaceutical compositions and methods for using said compounds and compositions.

11 Claims, No Drawings

DIASTEREOISOMERS OF N⁶-ENDO-BICYCLO[2.2.1]HEPTYLADENOSINE AS ANTIHYPERTENSIVES WITH SELECTIVE ACTION

BACKGROUND OF THE INVENTION $N^6$-endo-bicyclo[2.2.1]heptyl adenosine as a diastereomeric mixture, i.e., is disclosed in US Application Ser. No. 772,983, now U.S. Pat. No. 4,714,697, as having a favorable ratio of affinities at $A_1$ and $A_2$ receptors and highly desirable analgesic and antiinflammatory properties.

It is now found that eachof the 1R- and 1S-diastereomers of $N^6$-endo-bicyclo[2.2.1]heptyl adenosine has particularly unexpected $A_1$ and $A_2$ receptor binding ratios.

SUMMARY OF THE INVENTION

Accordingly the present invention is related to an $N^6$-endo-bicyclo[2.2.1]heptyl adenosine of the formula

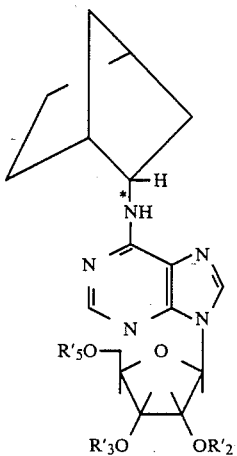

VII wherein * is an asymmetric carbon, particularly the endo form and more particularly the 1S- or 1R- form, and $R'_2$, $R'_3$, and $R'_5$ are each independently hydrogen, lower alkanoyl, benzoyl, or benzoyl mono substituted by lower alkyl, lower alkoxy, halogen, trifluoromethyl, or when $R^2$, and $R^3$, are taken together are alkylidene, preferably isopropylidene, or a pharmaceutically acceptable acid addition salt thereof.

The present invention also relates to a pharmaceutical composition comprising a therapeutically effective amount of a compound of the above formula VII with a pharmaceutically acceptable carrier. Finally, the present invention is also to a method of treating mammals by administering to such mammals a dosage form of a compound of the formula X

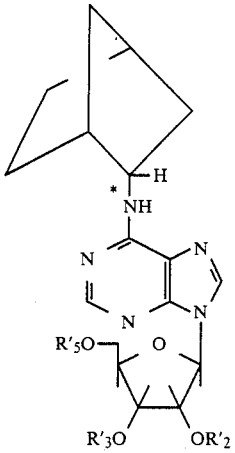

X a mixture or an individual diastereomer thereof; in which NH— is endo and $R'_2$, $R'_3$ and $R'_5$ are each independently H, lower alkyl, lower alkoxy, halogen or trifluoromethyl, or when $R'_2$ and $R'_3$ are taken together are lower alkylidene, or a pharmaceutically acceptable addition salt thereof.

That is, the compound of formula X is a diastereomeric mixture of the $N^6$-endo form, a 1R-endo or a 1S-endo stereoisomer of the compound of the formula X.

DETAILED DESCRIPTION OF THE EMBODIMENTS

In the compounds of the formula VII, the term "lower alkyl" is meant to include a straight or branched alkyl group having from 1 to 6 carbon atoms such as, for example, methyl, ethyl, propyl, isopropyl, butyl, sec-butyl, isobutyl, tert-butyl, amyl, isoamyl, neopentyl, hexyl, and the like.

Halogen includes particularly fluorine, chlorine or bromine.

Lower alkoxy is O-alkyl or S-alkyl of from 1 to 6 carbon atoms as defined above for "lower alkyl".

Lower alkanoyl is a straight or branched

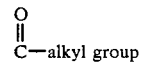

of from 1 to 6 carbon atoms in the alkyl chain as defined above.

The compounds of formula VII or X are useful both in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the invention contain asymmetric carbon atoms, and particularly, at the carbon atom adjacent to the NH moiety of the adenosine and at the two carbons at the terminal points of the CH$_2$ containing bridge of the bicycloheptyl moiety. The invention concerns the diastereomers when the carbon adjacent to the NH moiety is in the endo form. U.S. application Ser. No. 772,983 now U.S. Pat. No. 4,814,697 discloses a mixture of the endo form and is, therefore, incorporated by reference. More specifically, however, the present invention for the compound of formula VII and composition therefor concerns only each individual diastereomer having the 1R- or 1S- configuration. The individual diastereomer may be isolated or prepared by methods known in the art or as described herein.

A preferred embodiment of the present invention includes a compound of formula VII wherein $R'_2$, $R'_3$ and $R'_5$ are hydrogen, acetyl or benzoyl or when $R'_2$ and $R'_3$ are taken together form isopropylidene.

The more preferred embodiments are (1R-endo)-N$^6$-bicyclo[2.2.1]hept-2-yl adenosine and (1S-endo)-N$^6$-bicyclo[2.2.1]hept-2-yl adenosine.

The most preferred embodiment is (1S-endo)-N$^6$-bicyclo[2.2.1]hept-2-yl adenosine.

Generally, the compounds of formula VII may be conveniently synthesized by first preparing each of S (−)-norbornylamine of the formula VI and R (+)-norbornylamine of the formula VIa as follows using preparations as shown or preparations analogous to those as shown in the indicated references in the Schemes A and B respectively:

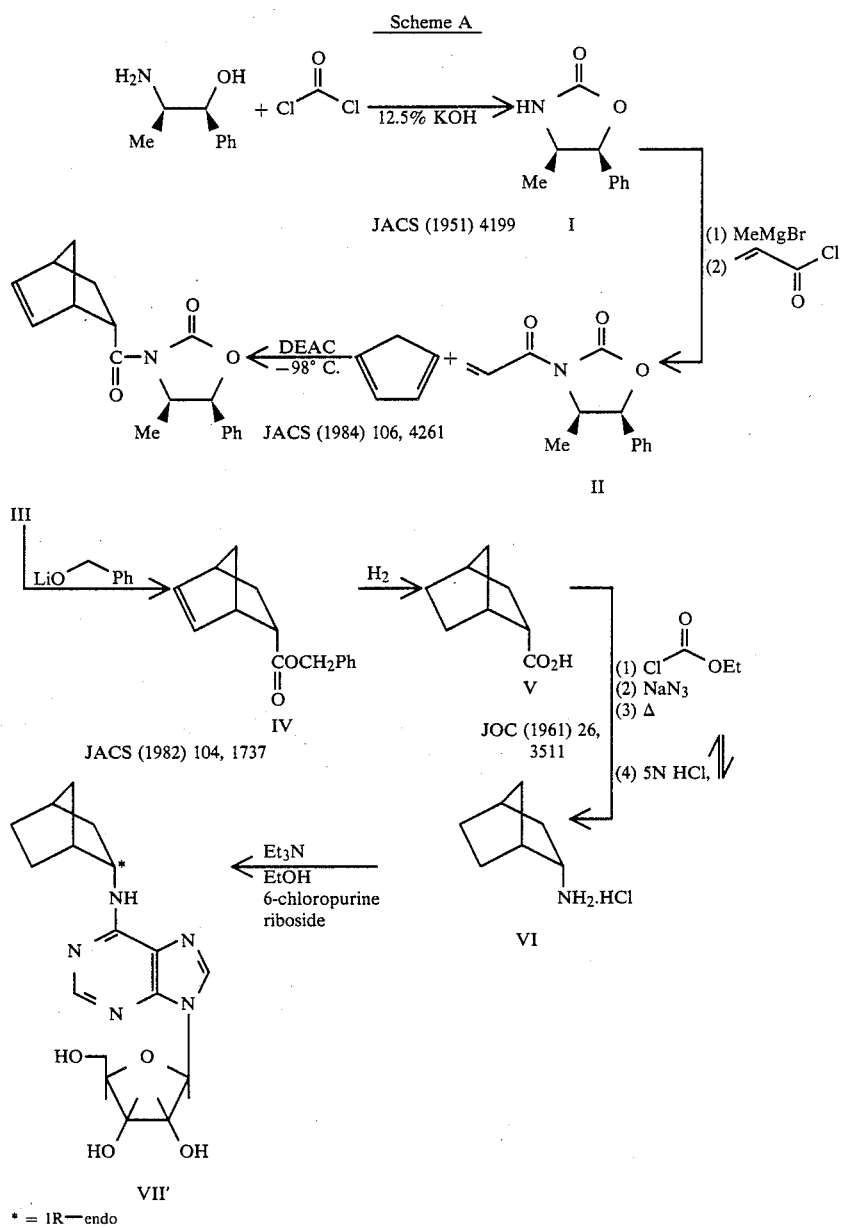

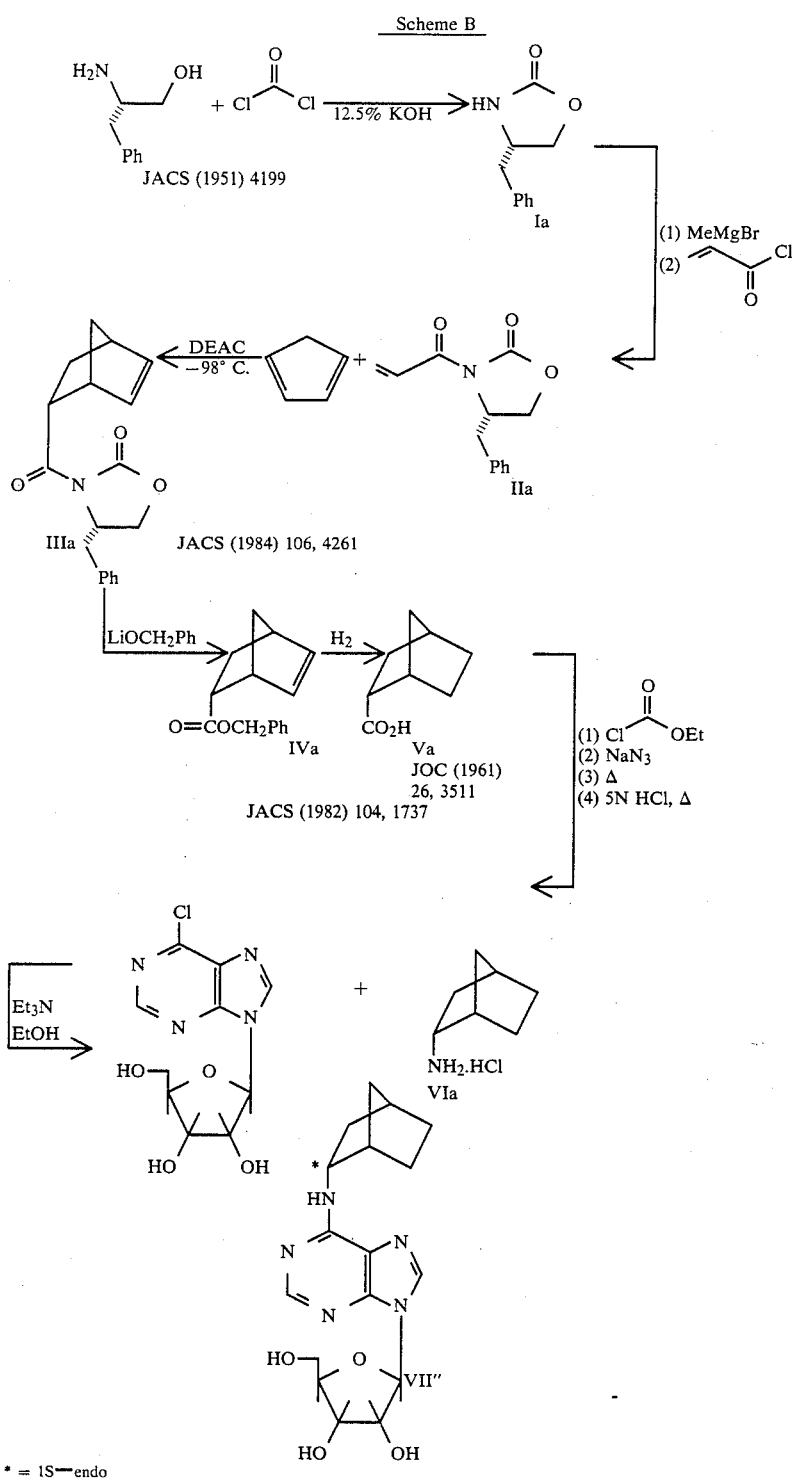

\* = 1S—endo

Although neither Scheme A nor Scheme B show the various definitions of R′$_2$, R′$_3$ and R′$_5$ as defined above, one of ordinary skill would realize that it may be convenient to protect the ribofuranose hydroxyl groups with esters according to the definitions of R′$_2$, R′$_3$ and R′$_5$ which may then be removed as desired.

The compounds of formula VII have been found to possess differing affinities for adenosine receptors (designated A$_1$ and A$_2$ receptors for convenience as accepted in the literature). Particularly, the ratios of A$_1$ to A$_2$ receptor binding for each are unexpected.

PHARMACOLOGICAL EVALUATION

The A$_1$ receptor affinity and A$_2$ receptor affinity of each is determined in the generally accepted assay for adenosine receptor binding as described in U.S. application Ser. No. 772,983 now U.S. Pat. No. 4,714,697 noted above and then ratios are subsequently calculated and compared to the diastereomeric mixture of endo-bicyclo[2.2.1]heptyl adenosine disclosed in U.S. application Ser. No. 772,983 now U.S. Pat. No. 4,714,697 with results as shown in the following Table 1.

TABLE 1

| Compound | n | A$_1$ IC$_{50}$ ± SE | n | A$_2$ IC$_{50}$ ± SE | A$_2$/A$_1$ Ratio |
|---|---|---|---|---|---|
| Diastereomeric mixture | 2 | 0.738 ± 0.088 | 3 | 1110 ± 145 | 1504 |
| Isomer VII' | 2 | 0.564 ± 0.061 | 1 | 2300 — | 4078 |
| Isomer VII" | 1 | 2.63 — | 1 | 1200 — | 456 |

Antihypertensive evaluation (AHP3) is carried out by a generally accepted assay as described in U.S. Pat. No. 4,626,526 for the representative compounds of formula X which are the diastereomeric mixture of endo-bicyclo[2.2.1]heptyl adenosine (Mixture) and each of Isomer VII' and Isomer VII" as defined above with the following results. The diastereomeric mixture, i.e. Mixture, of endo-bicyclo[2.2.1]heptyl adenosines is disclosed in US Application Ser. No. 772,983 issued as U.S. Pat. No. 4,714,697.

TABLE 2

|  | ED$_{40}$* |
|---|---|
| Mixture | 0.6 |
| Example 1 (VII') | 0.16 |
| Example 2 (VII") | 0.7 |

*Dose causing a 40 nm drop in blood pressure, mg/kg.

Accordingly the present invention is a pharmaceutical composition for treating hypertension in mammals, particularly humans, which comprises an antihypertensive amount of the compound of formula VII together with a pharmaceutically acceptable carrier.

The present invention further includes a method for treating hypertension in mammals, again particularly humans, suffering therefrom which comprises administering to such mammals either orally or parenterally a compound of the formula X as defined above in appropriate unit dosage form.

The preparation of pharmaceutical compositions from the compounds of this invention is within the ordinary skill of an artisan such as is described in U.S. Pat. Ser. No. 4,626,526 noted above.

The quantity of active compound in a unit dose of preparation may be varied or adjusted from 0.1 mg to 300 mg, preferably to 0.5 to 50 mg according to the particular application and the potency of the active ingredient. The compositions can, if desired, also contain other compatible therapeutic agents.

In therapeutic use as described above, the mammalian dosage range for a 70 kg subject is from 0.01 to 100mg/kg of body weight per day or preferably 0.1 to 50mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention.

EXPERIMENTAL

Preparation I (4R,5S)-4-Methyl-5-phenyl-2-oxazolidone (I): Cool a solution of 30.0 g (+)-(1S,2R)-norephedrine (0.16 mole, 1 eq) in 300 ml toluene and 400 ml 12.5% KOH solution (0.96 mole, 6eq) in an ice bath. Add 180 ml of 27% phosgene in toluene (0.50 mole, 3.1 eq) dropwise over a period of 15 minutes. Let is stir for an additional 15 minutes. Separate layers and dry organics over MgSO$_4$. Concentrate to obtain 26.3 g of a white solid. Recrystallize from 300 ml H$_2$O+50 ml EtOH. Collect white plates. Dissolve in CH$_2$CL$_2$ and dry over MgSO$_4$. Filter and concentrate.

20.4 g of a white powder with mp 119°-120° C. collected. 72% yield.

Analysis (C$_{10}$H$_{11}$NO$_2$): Calcd. C, 67.78; H, 6.26; N, 7.90 Found C, 67.38; H, 6.12; N, 7.78.

Preparation IA (4S-4-Benzyl-2-oxazolidone (Ia): Prepared as above. 45% yield. Mp 83°-84° C.

Analysis (C$_{10}$H$_{11}$NO$_2$): Calcd. C, 67.78; H, 6.26; N, 7.90 Found C, 67.51; H, 6.26; N, 7.74.

Reference: Newman, M.S., Kutner, A., J. Amer. Chem. Soc., 1951, 73, 4199.

Preparation II (4R,5S)-3-Propionyl-4-methyl-5-phenyl-2-oxazolidone (II):

Cool a solution of 5.00 g of I (0.028 mole, 1 eq) and ca. 30 mg of hydroquinone in 180 ml of THF to 0° C. under a nitrogen atmosphere. Add 9.1 ml of 3.0 M MeMgBr (0.027 mole, 0.97 eq) and stir at 0° C. for 10 minutes. 2.3 ml of acryloyl chloride (0.028, 1 eq) is added and the resulting solution allowed to stir for 5 minutes before pouring into a separatory funnel containing 200 ml Et$_2$O. Extract with aqueous NH$_4$Cl and dry organics over MgSO$_4$. Filter and concentrate to obtain 7.03 g of a yellow oil. Flash chromatography on silica gel using 2:1 hexane/Et$_2$O affords 4.30 g of a colorless oil. 66% yield. NMR (CDCl$_3$, δ), 7.35 (m) overlapping 7.50 (d of d, J=17.3, 10.5 Hz, total 6H), 6.50 (d of d, 1H, J=17.0, 1.8 Hz), 5.85 (d of d, 1H, J=10.4, 1.8 Hz), 5.70 (d, 1H, J=7.2), 4.80 (d of d (quint) J=6.6, 7.2 Hz), 0.93 (d, J=6.6, 3H).

Preparation IIA (4S-3-Propionyl-4-benzyl-2-oxazolidone (IIa):

Prepared as above from Ia and without the additionof hydroquinone. Flash chromatography on silica gel using 1:1 hexane/Et$_2$O yielded 2.97 g of a white solid. Mp 73° C. NMR (CDCl$_3$, δ), 7.55 (d of d, 1H, J=17.0, 10.5 Hz), 7.30 (m, SH), 6.60 (d of d, 1H, J=17.0, 1.8 Hz), 5.95 (d of d, 1H, J=10.5, 1.8 Hz), 4.70 (m, 1H), 4.25 (m, 2H), 3.35 (d of d, 1H, J=13.4, 3.2 Hz), 2.80 (d of d, 1H, J=13.4, 9.6 Hz). Reference: Evans, D. A., Chapman, K. T.; Bisaha, J., J. Amer. Chem. Soc., 1984, 106, 4261.

Preparation III

Cycloaddition of II with cyclopentadiene (III):

Precool a solution containing 2.13 g of II (9.2 mmole, 1 eq) in 150 ml CH$_2$Cl$_2$ under nitrogen to −78° C. in a dry ice/acetone bath for 15 minutes before placing in N$_2$(1)/MeOH bath at −98° C. Cool at −98° C. for 20 minutes. Add 5.6 ml 1.8 M DEAC (10.1 mmole, 1.1 eq)

and immediately follow with excess cyclopentadiene (7 ml, freshly cracked) precooled to −78° C. Stir for 5 minutes at −98° C. and then pour into 1N HCl. Extract twice with $CH_2Cl_2$. Combine organics and dry over $MgSO_4$. Filter and concentrate. Flash chromatography on silica gel performed using 20% EtOAc in hexane. Collected 1.86 g of white solid. Mp 82.5°–85° C. 68% yield.

Preparation IIIA

Cycloaddition of IIa with cyclopentadiene (IIIa):

Prepared as detailed above. Flash chromatography performed on silica gel using 20% EtOAc in hexane. White solid collected which was then recrystallized from 1:20 EtOAc/hexane. White needles collected, dried for 1 hour in vacuum oven at room temperature. 46% yield. Mp 120°–121° C. Reference: Evans, D. A.; Chapman, K. T.; Bisaha, J., J. Amer. Chem. Soc., 1984, 106, 4261.

Preparation IV (−)-(1S,2S,4S)-endo-2-Carbobenzyloxy-5-norbornene (IV):

Dissolve 1.3 ml benzyl alcohol (12.1 mmole, 2 eq) in 45 ml of THF and cool to 0° C. under a nitrogen atmosphere. Add 3.5 ml 2.6M n-BuLi (9.1 mmole, 1.5 eq) and let it stir for 15 minutes. Add 1.83 g of III (6.2 mmole, 1 eq) dissolved in 10 ml of THF and stir at 0° C. for 2 hours. Pour into water and extract twice with $CH_2Cl_2$. Dry over $MgSO_4$, filter and concentrate. Flash chromatography on silica gel performed using 10% EtOAc in hexane. 1.16 g of a colorless oil collected. 83% yield. $[\alpha]_D$−113.1° C. (C, 0.14, $CHCl_3$).

Preparation IVA (+)-(1R,2R,4R)-endo-2-Carbobenzyloxy-5-norbornene (IVa):

Prepared as above. Flash chromatography on silica gel using 10% EtOAc/hexane gave a colorless oil in 79% yield. $[\alpha]_D$+119.3 (C, 1.36, $CHCl_3$). Reference: Evans, D. A.; Ennis, M. D.; Mathre, D. J., J. Amer. Chem. Soc., 1982, 104, 1737. Reference for rotations: Evans, D. A.; Chapman, K. T., Bisaha, J., J. Amer. Chem. Soc., 1984, 106, 4261.

Reported for (−) isomer: $[\alpha]_D$−133.9° C. (C, 1.37, $CHCl_3$) for (+) isomer: $[\alpha]_D$+133.9° C. (C, Preparation V (−)-(1R,2S,4S)-endo-Norbornane-2-carboxylic acid (V):

Add 0.2 g 20% Pd/C to a solution of 1.13 g of IV (50 mmole) in 100 ml THF. Place in Parr shaker under 50.5 psi of hydrogen at room temperature for 2 hours. The theoretical amount of hydrogen was taken up at this time and the catalyst filtered off. Concentration of filtrate yielded a yellow oil which was Kugel Rohr distilled (0.2 mmHg, 75°–85° C.). 0.53 g of a colorless oil was obtained. 76% yield. $[\alpha]_D$−25.0° C. (C, 1.00, EtOH).

Preparation VA (+)-(1S,2R,4R)-endo-Norbornane-2-carboxylic acid (Va):

Prepared as described for V. After distillation a 99% yield of a colorless oil was obtained.

Preparation VI (−)-(1R,2S,4S)-endo-2-Aminonorbornane.HCl (VI):

Suspend 0.52 g of V (3.7 mmole, 1 eq) in 0.6 ml $H_2O$ and add acetone until dissolution. Cool to 0° C. and add 0.6 ml $Et_3N$ (4.5 mmole, 1.2 eq) dissolved in 8 ml acetone. Add 0.46 ml freshly distilled ethyl chloroformate (4.8 mmole, 1.3 eq) dissolved in 2 ml acetone and stir for 30 minutes. Add 0.36 g $NaN_3$ (5.6 mmole, 1.5 eq) dissolved in 1.3 ml $H_2O$ and stir for an additional hour at 0° C. Pour into ice water and extract with toluene. Dry organics over $MgSO_4$ and filter. Add filtrate dropwise to a flask heated on a steam bath. Addition takes about 15 minutes. Concentrate. Reflux recovered oil in 5 ml of 5N HCl for 9 hours and concentrate. Add 40% NaOH to flask and extract with $Et_2O$. Dry organics over $MgSO_4$, filter. Add saturated EtOH/HCl to the filtrate and filter to collect white powder. Dry in vacuum oven for 1 hour at room temperature. 159.2 mg obtained. 29% yield. Mp .250° C. IR (KBr, $cm^{-1}$) 2900, 1601, NMR (DMSO-$d_6$, δ), 8.10 (broad, 2H), 2.40 (br s, 1H), 2.20 (br s, 1H), 1.92 (m, 1H), 1.7–1.3 (m, 5H), 0.97 (m, 1H).

Preparation VIA (+)-(1S,2R,4R)-endo-2-Aminonorbornane.HCl (VIa):

Prepared as in above procedure in 37% yield. $[\alpha]_D$+4.4° C. (C, 1.02, EtOH). IR (KBr, $cm^{-1}$) 2900, 1601, NMR (DMSO-$d_6$, δ), 8.10 (broad, 2H), 3.40 (m, 1H), 2.40 (br s, 1H), 2.20 (br s, 1H), 1.92 (m, 1H), 1.7–1.3 (m, 5H), 0.97 (m, 1H).

EXAMPLE 1

(1R-endo)-N-Bicyclo[2.2.1]hept-2-yl adenosine (VII′):

Reflux 0.114 mg of VI (1.05 mmole, 1.1eq) in 10 ml EtOH with 0.27 g 6-chloropurine riboside (0.95 mmole, 1 eq) and 0.3 ml $Et_3N$ (2.38 mmole, 2.5 eq) for 12 hours and concentrate. Flash chromatography on silica gel using 10% MeOH in $CH_2Cl_2$ performed. 210 mg of a white powder obtained as a $CH_2Cl_2$ salt (1:1). Mp 131°–133° C. 45% yield. $[\neq 0]_D$−77.3° C. (C, 0.66, EtOH).

Analysis for $C_{17}H_{23}N_5O_4.CH_2Cl_2$: Calcd. C, 48.44; H, 5.64; N, 15.69 Found C, 48.71; H, 5.63; N, 15.74.

EXAMPLE 2

(1S-endo)-N-Bicyclo[2.2.1]hept-2-yl adenosine (VII″):

Prepared as above in 76% yield as a $CH_2Cl_2$ salt. Mp 123°–130° C. $[\alpha]_D$−27.6° C. (C, 0.64, EtOH).

Analysis for $C_{17}H_{23}N_5O_4.0.35\ CH_2Cl_2$ Calcd. C, 53.28; H, 6.11; N, 17.91 Found C, 53.34; H, 6.14; N, 17.92.

I claim:

1. A compound of the formula

VII

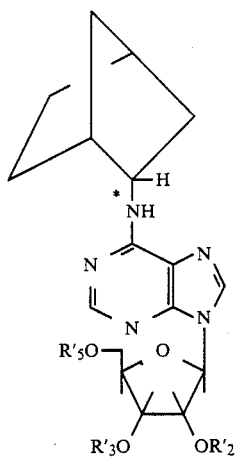

wherein the stereoisomeric form is 1R-endo or 1S-endo, and $R'_2$, $R'_3$ and $R'_5$ are each independently H, lower alkanoyl, benzoyl, benzoyl substituted by lower alkyl, lower alkoxy, halogen or trifluoromethyl, or when $R'_2$ and $R'_3$ are taken together are lower alkylidene, or a pharmaceutically acceptable acid addition salt thereof.

2. A compound of claim 1 which is (1R-endo)-N-bicyclo[2.2.1]hept-2-yl adenosine.

3. A compound of claim 2 that is the dichloromethylene salt of the compound.

4. A compound of claim 1 which is (1S-endo)-N-bicyclo[2.2.1]hept-2-yl adenosine.

5. A compound of claim 4 that is the dichloromethylene salt of the compound.

6. A pharmaceutical composition for treating hypertension which comprises an antihypertensive amount of the compound of claim 1 with a pharmaceutically acceptable carrier.

7. A method for treating hypertension in a human suffering therefrom which comprises administering the compound of formula X

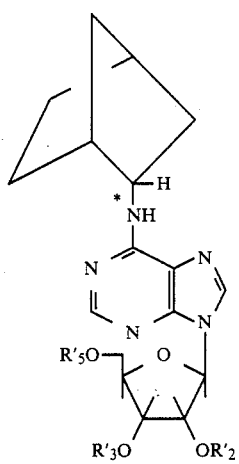

a mixture or an individual diastereomer thereof; in which NH— is endo and $R'_2$, $R'_3$ and $R'_5$ are each independently H, lower alkyl, lower alkoxy, halogen or trifluoromethyl, or when $R'_2$ and $R'_3$ are taken together are lower alkylidene, or a pharmaceutically acceptable addition salt thereof in a unit dosage form.

8. A method according to claim 7 wherein the compound X is a mixture of the $N^6$-endo form of X that is diastereoemers of compound X.

9. A method according to claim 8 wherein the compound X is the mixture of stereoisomers of $N^6$-endo-bicyclo[2.2.1]heptyl adenosine.

10. A method according to claim 9 wherein the compound X is (1R-endo)-N-bicyclo[2.2.1]hept-2-yl adenosine.

11. A method according to claim 9 wherein the compound X is (1S-endo-)-N-bicyclo[2.2.1]hept-2-yl adenosine.

* * * * *

UNITED STATES PATENT AND TRADEMARK OFFICE
CERTIFICATE OF CORRECTION

PATENT NO. : 4,837,207
DATED : June 6, 1989
INVENTOR(S) : B.K. Trivedi

It is certified that error appears in the above—identified patent and that said Letters Patent is hereby corrected as shown below:

```
In column 11 line 21 before "wherein" add
-- wherein * consists of an asymmetric
carbon --.
```

Signed and Sealed this

Sixth Day of February, 1990

*Attest:*

JEFFREY M. SAMUELS

*Attesting Officer*  *Acting Commissioner of Patents and Trademarks*